(12) United States Patent
Praus

(10) Patent No.: US 9,109,990 B2
(45) Date of Patent: Aug. 18, 2015

(54) METHOD FOR ASCERTAINING AN ADHESION CONDITION OF A FRICTION CLUTCH

(71) Applicant: Schaeffler Technologies AG & Co. KG, Herzogenaurach (DE)

(72) Inventor: Rainer Praus, Ottersweier (DE)

(73) Assignee: Schaeffler Technologies AG & Co. KG, Herzogenaurach (DE)

( * ) Notice: Subject to any disclaimer, the term of this patent is extended or adjusted under 35 U.S.C. 154(b) by 301 days.

(21) Appl. No.: 13/863,575

(22) Filed: Apr. 16, 2013

(65) Prior Publication Data

US 2013/0276525 A1 Oct. 24, 2013

(30) Foreign Application Priority Data

Apr. 18, 2012 (DE) .......................... 10 2012 206 342

(51) Int. Cl.
*G01N 19/04* (2006.01)
*F16D 13/00* (2006.01)
*F16D 48/00* (2006.01)

(52) U.S. Cl.
CPC ................ *G01N 19/04* (2013.01); *F16D 13/00* (2013.01); *F16D 48/00* (2013.01)

(58) Field of Classification Search
CPC . F16D 13/00; F16D 48/00; F16D 2500/1045; F16D 2500/70426; F16D 2500/70663; F16D 2500/5012; G01N 19/04; G01M 13/02
USPC ........................................................ 73/150 A
See application file for complete search history.

(56) References Cited

U.S. PATENT DOCUMENTS

| | | | | |
|---|---|---|---|---|
| 7,416,068 | B2 * | 8/2008 | Ray et al. ..................... | 192/82 T |
| 7,813,858 | B2 * | 10/2010 | Praus et al. .................... | 701/68 |
| 2006/0148616 | A1 * | 7/2006 | Ray et al. ..................... | 477/175 |
| 2010/0094518 | A1 * | 4/2010 | Praus et al. .................... | 701/68 |
| 2012/0211323 | A1 * | 8/2012 | Goeppert .................... | 192/84.6 |

FOREIGN PATENT DOCUMENTS

DE 102009029741 1/2010

* cited by examiner

*Primary Examiner* — Freddie Kirkland, III
(74) *Attorney, Agent, or Firm* — Simpson & Simpson, PLLC

(57) ABSTRACT

A method for ascertaining an adhesion condition of a friction clutch operated with specified slip between an input part and an output part. In the case of rotational speed differences in the range of noise in the latter, a mean value and its variance are continuously derived from measurements taken by an unfiltered rotational speed difference between the input part and the output part, and when the mean value falls below a specified threshold and simultaneously the variance exceeds the mean value, the adhesion condition is recognized.

8 Claims, 1 Drawing Sheet

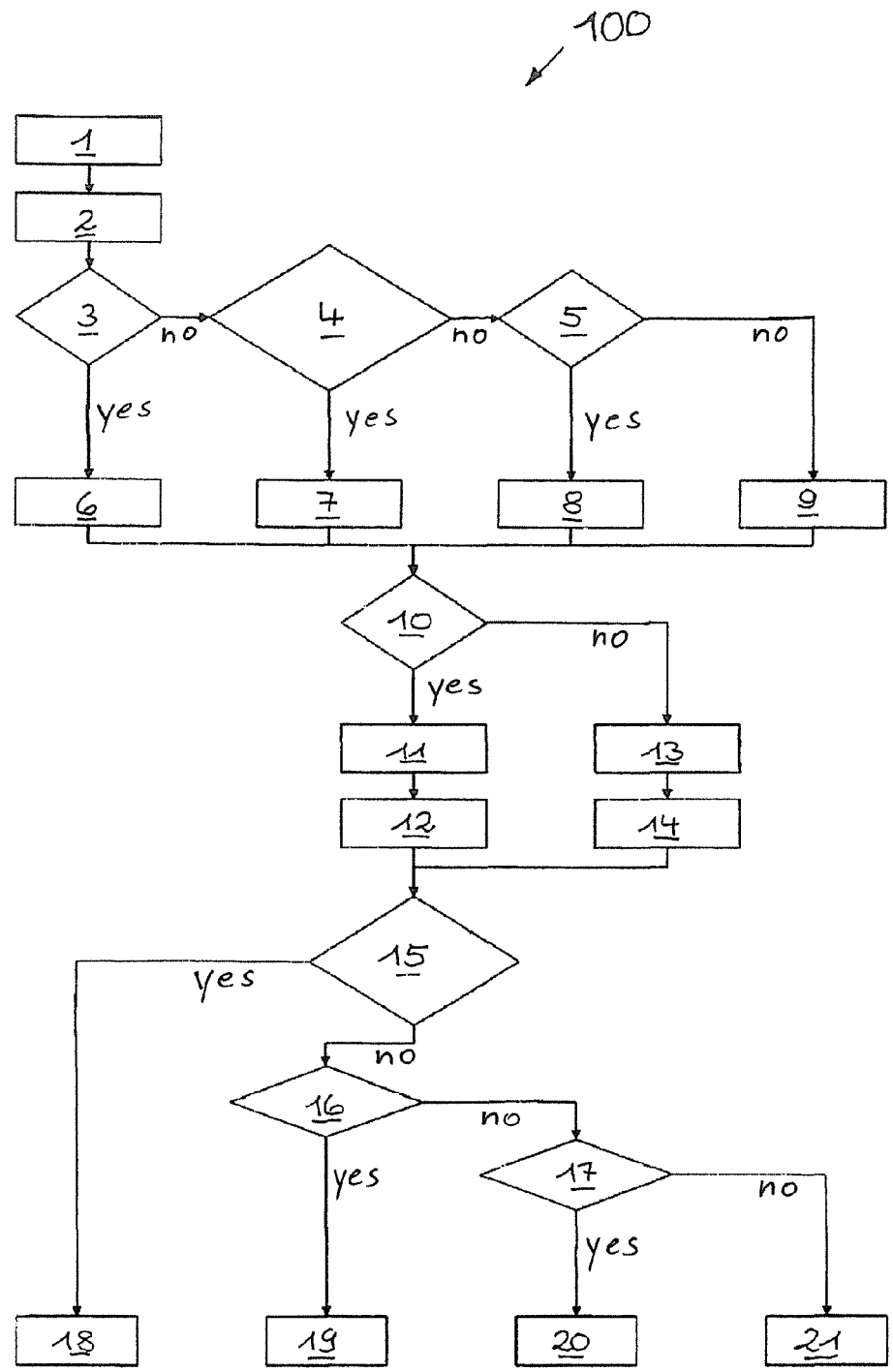

METHOD FOR ASCERTAINING AN ADHESION CONDITION OF A FRICTION CLUTCH

CROSS-REFERENCE TO RELATED APPLICATIONS

This application claims priority from German Patent Application No. 10 2012 206 342.0 filed Apr. 18, 2012, which application is incorporated herein by reference in its entirety.

FIELD OF THE INVENTION

The invention relates to a method for ascertaining an adhesion condition of a friction clutch operated with specified slip between an input part and an output part.

BACKGROUND OF THE INVENTION

A relevant friction clutch is utilized in drivetrains between an internal combustion engine and a transmission, and controls the torque transmissible from the internal combustion engine to the transmission. If the transmission is designed as a dual-clutch transmission, then a friction clutch of this type is situated between each sub-transmission of the dual-clutch transmission and the internal combustion engine. When the friction clutch is in the engaged state, it transmits the maximum transmissible torque, including the torque peaks of the internal combustion engine which occur as a result of its rotational irregularities. In corresponding control methods of such friction clutches automated by means of a clutch actuator, these friction clutches are not engaged at the maximum torque, but are operated at a specified slip dependent on the driving situation, at which a rotational speed difference is regulated between the input part, which is connected to the crankshaft, and the output part of the friction clutch, which is connected to a transmission input shaft of the transmission, at which speed difference the torque peaks of the combustion engine are not transmitted, or only partially transmitted. This causes a damping of the torsional vibrations that occur in the drivetrain. In this connection, an unambiguous assignment of a slip condition and an adhesion condition is necessary in the control system of the friction clutch and in the transmission, for example, for adaptation processes of the friction clutch and shifting points of the transmission. To differentiate between a slip and an adhesion condition, a minimum slip with rotational speed differences between the input and output part of, for example, less than 50 revolutions per minute (rpm) is recognized as the transition from a slip condition to an adhesion condition. Such slight rotational speed differences are advantageous on the one hand for damping torque peaks, but on the other hand are overlaid by noise and vibration disturbances, so that detection of an adhesion condition is difficult.

German Patent No. 10 2009 029 741 A1 shows the adhesion condition of a friction clutch on the basis of a command variable that is traced back to the existing clutch torque.

BRIEF SUMMARY OF THE INVENTION

The object of the invention is to refine a method for recognizing an adhesion condition of a friction clutch.

The object is fulfilled by a method for ascertaining an adhesion condition of a friction clutch operated with specified slip between an input part and an output part, wherein a mean value and its variance are continuously derived from measurements taken by means of an unfiltered rotational speed difference between the input part and the output part, and when the mean value falls below a specified threshold and simultaneously the variance exceeds the mean value, the adhesion condition is recognized. The rough rotational speed difference which reflects the slip is continuously averaged here and the error in the mean value is determined. If the mean value becomes smaller due to decreasing slip, the adhesion condition is recognized if the error bar of the mean value includes the value zero.

In normal determinations of the mean value, the error in the mean value rises faster than the mean value itself, in particular with major changes in the slip, so that the adhesion condition may be recognized erroneously. In order to prevent this, the measurements are acquired within equidistant time intervals on the basis of a continuous counter, while a current mean value is obtained from a previous mean value derived from a number of measurements determined on the basis of the counter, and a newly acquired measurement. The mean value is initialized in this case by resetting the counter, if a change in a last variance compared to a last prior variance of the mean value exceeds a specified limit. In this case, a valid mean value is obtained in a preferred manner only if a mean value has been derived from a specified number of measurements, in order to achieve adequate statistical reliability of the mean value and its variance.

In a preferred manner, a mean value $\bar{x}_n$ from the number n of measurements $x_n$ of the rotational speed difference acquired at equidistant time intervals is obtained from the speed of rotation of the input part, for example, the engine speed, and the speed of rotation of the output part, for example, the speed of the transmission input shaft. The current mean value $\bar{x}_{n+1}$ is obtained from the mean value $\bar{x}_n$ with allowance for the currently acquired mean value $x_{n+1}$ according to equation (1) as follows:

$$\bar{x}_{n+1} = \bar{x}_n + \frac{1}{n+1}(x_{n+1} - \bar{x}_n).$$

The pertinent current variance $\sigma_{n+1}^2$ is obtained corresponding to the current mean value $\bar{x}_{n+1}$ from the corresponding variance $\sigma_n^2$ according to equation (2) as follows:

$$\sigma_{n+1}^2 = \frac{n}{n+1}\left(\sigma_n^2 + \frac{(x_{n+1} - \bar{x}_n)^2}{n+1}\right).$$

In this case, with the friction clutch completely engaged and a positive rotational speed difference, an erroneous determination of the adhesion condition may be made, since the mean value remains constant over an extended time and therefore over a rather large number of measurements, and the variance is very small. In this case, no notice is issued, for example, by a control device of the friction clutch, that the friction clutch is engaged. This means that sequences, procedures and the like which follow this notification of the engaged friction clutch cannot be started. In order to prevent such an erroneous determination, when these operating conditions are present with the friction clutch engaged, an adhesion condition can be recognized if the mean value falls below a limiting value.

BRIEF DESCRIPTION OF THE DRAWINGS

The nature and mode of operation of the present invention will now be more fully described in the following detailed description of the invention taken with the accompanying drawing figure, in which:

FIG. 1 is a block diagram of a method for recognizing an adhesion condition of an automated friction clutch.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

The flow sequence of FIG. 1 shows block diagram 100. The diagram starts in Block 1 with the determination of the variance difference $\Delta\sigma_n^2$ of the current variance $\sigma_{n+1}^2$ obtained according to equation (2) compared to the prior variance $\sigma_n^2$ from the ongoing acquisition and calculation of measurements of the speeds of rotation of the input part and the output part of the friction clutch, calculation of the differences between the latter, and determination of the mean value $\bar{x}_n$, $\bar{x}_{n+1}$ at spaces of a time interval with increasing number n. These, as well as the variance deviation compared to the variance $\sigma_n^2$ are saved in Block 2. In Branch 3 a check is performed to determine whether the number n of measurements for recognizing an adhesion condition is greater than a minimum number n(min) for sufficiently precise determination of the adhesion condition. If the number of measurements is too low, the counter for counting the number n is incremented in Block 6. If the number of measurements in the branch is greater or equal to the minimum number, in Branch 4 a check is performed to determine whether the variance difference $\Delta\sigma_n^2$ is greater than a specified limiting value S1, or the slip difference $\Delta s$ in the form of a difference in the mean values $\bar{x}_n$, $\bar{x}_{n+1}$ is greater than a specified limiting value S2, or the slip in the form of the mean value $\bar{x}_{n+1}$ is greater than a specified limiting value S3. If this is the case, the counter is set to a starting value n(st). If this is not the case, in Branch 5 a check is performed to determine whether the number n is smaller than a maximum usable number n of measurements. If this is the case, the counter is incremented in Block 8. If this is not the case, the counter is set to the number n(min).

Blocks 6, 7, 8, 9 are followed by Branch 10, in which a check is performed to determine whether the counter is greater than the starting value n(st). If this is the case, in Block 11 the current mean value $\bar{x}_{n+1}$ is determined according to equation (1) and in Block 12 the current variance $\Sigma_{n+1}^2$ is determined according to equation (2). If this is not the case, in Block 13 the current mean value $\bar{x}_{n+1}$ is set equal to the currently acquired measurement n+1 and in Block 14 the current variance $\sigma_{n+1}^2$ is set to zero.

Subsequent to Blocks 12 and 14, in Branch 15 a check is performed to determine whether the mean value $\bar{x}_{n+1}$ is greater than a specified limiting value S4, or whether the number n is smaller than n(min), or whether the slip difference $\Delta s$ is greater than a specified limiting value S5. If this is the case, in Block 18 a flag is set to FALSE, which means that no adhesion is present. If this is not the case, in Branch 16 a check is performed to determine whether the current variance $\sigma_{n+1}^2$ is greater than the square of the current mean value $\bar{x}_{n+1}$. If this is the case, in Block 20 a flag is set to TRUE, which means that the adhesion condition of the friction clutch is present. If this is not the case, in Branch 17 a check is performed to determine whether the mean value $\bar{x}_{n+1}$ falls within an uncertainty value, for example with engaged friction clutch and positive slip with constant mean value and small variance. If this is the case, the flag in Block 20 is set to TRUE. If this is not the case, the flag is set to FALSE.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

LIST OF REFERENCE NUMERALS 1 block
2 block
3 branch
4 branch
5 branch
6 block
7 block
8 block
9 block
10 branch
11 block
12 block
13 block
14 block
15 branch
16 branch
17 branch
18 block
19 block
20 block
21 block
100 block diagram

What is claimed is:

1. A method for ascertaining an adhesion condition of a friction clutch operated with specified slip between an input part and an output part, comprising the following steps:
    deriving a mean value and its variance continuously from measurements taken by means of an unfiltered rotational speed difference between said input part and said output part; and,
    when said mean value falls below a specified threshold and simultaneously said variance exceeds said mean value, recognizing said adhesion condition.

2. The method recited in claim 1, wherein said measurements are obtained within equidistant time intervals on the basis of a continuous counter.

3. The method recited in claim 2, wherein a current mean value is derived from a prior mean value derived from said measurements obtained on the basis of said counter, and a currently obtained measurement.

4. The method recited in claim 3, wherein said counter is reset if a change in a last variance compared to a last prior variance of the mean value exceeds a specified limit.

5. The method recited in claim 2, wherein a mean value is obtained when a specified number of measurements is exceeded.

6. The method recited in claim 1, wherein said mean value is obtained according to the formula $$\bar{x}_{n+1} = \bar{x}_n + \frac{1}{n+1}(x_{n+1} - \bar{x}_n).$$

7. The method recited in claim 1, wherein said variance is obtained according to the formula $$\sigma_{n+1}^2 = \frac{n}{n+1}\left(\sigma_n^2 + \frac{(x_{n+1} - \bar{x}_n)^2}{n+1}\right).$$

8. The method recited in claim 1, wherein an adhesion condition is recognized when the friction clutch is completely engaged and a mean value falls below a limiting value.

* * * * *